United States Patent
Mahajan

(10) Patent No.: US 6,921,733 B2
(45) Date of Patent: Jul. 26, 2005

(54) LIQUID PHASE LOW TEMPERATURE METHOD FOR PRODUCTION OF METHANOL FROM SYNTHESIS GAS AND CATALYST FORMULATIONS THEREFOR

(75) Inventor: Devinder Mahajan, South Setauket, NY (US)

(73) Assignee: Brookhaven Science Associates, LLC, Upton, NY (US)

(*) Notice: Subject to any disclaimer, the term of this patent is extended or adjusted under 35 U.S.C. 154(b) by 66 days.

(21) Appl. No.: 10/046,603

(22) Filed: Jan. 16, 2002

(65) Prior Publication Data

US 2003/0158270 A1 Aug. 21, 2003

(51) Int. Cl.⁷ .................. B01J 31/00; B01J 37/00; C08F 4/02; C08F 4/60
(52) U.S. Cl. ........................ 502/103; 518/700
(58) Field of Search ........................ 502/103; 518/700

(56) References Cited

U.S. PATENT DOCUMENTS

| | | | |
|---|---|---|---|
| 4,619,946 A | * 10/1986 | Sapienza et al. | 518/700 |
| 4,935,395 A | 6/1990 | Mahajan et al. | |
| 4,992,480 A | * 2/1991 | Mahajan et al. | 518/700 |
| 5,238,895 A | * 8/1993 | Marchionna et al. | 502/169 |
| 6,248,796 B1 | 6/2001 | Jackson et al. | 518/714 |
| 6,596,423 B2 | * 7/2003 | Mahajan | 429/17 |

* cited by examiner

Primary Examiner—J. A. Lorengo
Assistant Examiner—Jennine Brown
(74) Attorney, Agent, or Firm—Margaret C. Bogosian

(57) ABSTRACT

The invention provides a homogenous catalyst for the production of methanol from purified synthesis gas at low temperature and low pressure which includes a transition metal capable of forming transition metal complexes with coordinating ligands and an alkoxide, the catalyst dissolved in a methanol solvent system, provided the transition metal complex is not transition metal carbonyl. The coordinating ligands can be selected from the group consisting of N-donor ligands, P-donor ligands, O-donor ligands, C-donor ligands, halogens and mixtures thereof.

20 Claims, No Drawings

LIQUID PHASE LOW TEMPERATURE METHOD FOR PRODUCTION OF METHANOL FROM SYNTHESIS GAS AND CATALYST FORMULATIONS THEREFOR

This invention was made with Government support under contract number DE-AC02-98CH10886, awarded by the U.S. Department of Energy. The Government has certain rights in the invention.

BACKGROUND OF THE INVENTION

1. Field of Invention

This invention relates to homogenous catalyst formulations for methanol production from synthesis gas and methods of producing methanol by using the catalyst formulations of the invention.

2. Description of the Related Art

The transport of natural gas from remote sites such as deposits embedded in the permafrost or methane hydrates beneath the ocean floor continues to present a technological challenge. The transport of compressed natural gas under pressure such as or of liquefied natural gas via liquefaction offer limited applications for the transportation of natural gas located at remote sites. As a result, the conversion of natural gas into transportable liquid fuel at the well-head is an attractive option. Under the gas-to-liquid option, natural gas is first converted into synthesis gas, which is primarily a mixture of $CO$, $CO_2$, $H_2$. The synthesis gas can subsequently be processed catalytically into either hydrocarbons via Fischer-Tropsch technology or methanol. Both the Fisher-Tropsch technology and methanol synthesis are commercially practiced but the carbon monoxide conversion efficiency remains an issue. Therefore, there is still a need for an improved yet economical gas-to-liquid process for use in facilitating the transportation of natural gas from remote sites.

Methanol can be manufactured by catalytic hydrogenation of carbon monoxide as shown in reaction [1]:

$$CO + 2H_2 \Leftrightarrow CH_3OH \; \Delta H = -128.6 \; kJ.mol^{-1} \qquad [1]$$

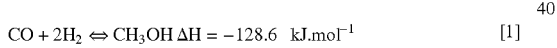

The operating temperature controls the CO conversion in this highly exothermic, reaction. Conventional commercial heterogeneous catalysts operate at approximately 250° C. and high pressure of about 750 psi and are limited by low equilibrium conversion that thermodynamically allows less than 20% conversion per pass of CO.

U.S. Pat. Nos. 4,935,395 and 4,992,480 incorporated herein by reference, describe two component catalyst systems consisting of tetracarbonyl nickel $Ni(CO)_4$ and alkali metal alkoxide of alkali metals such as Li, Na, K, Cs. More specifically, these patents disclose a catalyst system consisting of $Ni(CO)_4$ and potassium methoxide dissolved in a methanol solvent and a co-solvent such as tetrahydrofuran or p-dioxane. The catalyst system operates preferably between 100°–150° C. At these mild temperatures, per pass conversion of greater than 90% is achieved to yield methanol from synthesis gas with a $H_2/CO$ ratio of 2/1.

However, the system disclosed in these patents has two significant limitations. First, $Ni(CO)_4$, must be handled with a great deal of caution because it is quite toxic, having an OSHA limit of 1 ppb. Secondly, impurities in the synthesis gas ("syngas") such as $CO_2$ and $H_2O$ interact with the alkoxide base slowly leading to the deactivation of the catalyst system. As a result, the removal of $CO_2$ from the synthesis gas prior to it entering the methanol synthesis reactor renders the catalyst systems described above economically unattractive.

The cause of the deactivation of the catalyst is primarily due to interaction of the alkoxide base with $CO_2$ and $H_2O$ via reactions [2] and [3] respectively:

$$KOCH_3 + CO_2 \rightarrow KOCO_2CH_3 \qquad [2]$$

$$KOCH_3 + H_2O \rightarrow KOH + CH_3OH \qquad [3]$$

Alternately, synthesis gas entering the methanol synthesis reactor must be purified to remove these impurities to ppm level thus adding to the process cost. Reversing Reactions [2] and [3] will yield active $KOCH_3$, a process that facilitates methanol synthesis.

It is also recognized that the undesirable reaction of $KOCH_3$ with $CO_2$ to yield potassium methyl carbonate ($KOCO_2CH_3$ or PMC) as shown in Reaction 2 is exothermic and readily proceeds at room temperature. The equilibrium constant ($K_{eq}$) of this reaction is reported to be $2 \times 10^8$ $M^{-1}$ at 0° C. for sodium methoxide (C. Faurholt. Z. Physik. Chem. 126, pp. 72, 85, 211, 227 (1927)). This reaction ties up $KOCH_3$ that is needed to activate CO thereby disrupting the Ni-catalyzed methanol synthesis cycle when synthesis gas containing CO, $CO_2$, $H_2$ is used directly without prior $CO_2$ removal. Furthermore, $CO_2$ can be subsequently processed via the water-gas-shift ("WGS") reaction to yield CO for conversion to methanol.

$$H_2 + CO_2 \rightarrow CO + H_2O \qquad [4]$$

OBJECT OF THE INVENTION

It is, therefore, an object of the present invention to provide catalyst formulations that operate at low temperatures and pressures and are non-toxic.

It is another object of the present invention to provide catalyst formulations that can be used to produce methanol from synthesis gas containing $CO_2$ and other impurities.

SUMMARY OF THE INVENTION

The present invention, which addresses the needs of the prior art, provides a homogenous catalyst for the production of methanol from purified synthesis gas at low temperature and pressures which includes a transition metal capable of forming transition metal complexes with coordinate ligands, and an alkoxide, the catalyst being dissolved in a methanol solvent system provided, however, that the transition metal complex is not a transition metal carbonyl. The coordinate ligands can be selected from the group consisting of N-donor ligands, P-donor ligands, O-donor ligands, C-donor ligands, halogens and mixtures thereof. In one aspect of the invention the homogenous catalyst includes a transition metal complex which is a nontoxic material having C-donor ligands, provided that at least one C-donor ligand is other than carbonyl. The synthesis gas can include $CO_2$, CO or $H_2$.

The catalyst components of the homogenous catalyst are completely dissolved in the methanol solvent to yield a homogenous liquid solution. The transition metal is a metal from Group 6, Group 8, Group 9, Group 10, Group 11, Group 12 or mixtures thereof. Preferably, the transition metal is Mo, W, Fe, Ru, Os, Co, Rh, Ir, Ni, Pd, Pt, Cu, Au, Zn, Cd, or mixtures thereof. More preferably, the transition metal is selected from the Group consisting of Ni, Pd, Mo, Cu, Ru, Fe, or mixtures thereof.

Useful ligands for the transition metal complex of the homogenous catalyst are preferably selected from the group consisting of chloride, acetylacetonate, 2,2-dipyridyl, bis (cyclooctadiene), 1,10-phenanthroline, 1,2-bis (diphenylphosphinoethane) and mixtures thereof.

In the catalyst of the present invention, the metal alkoxide is derived from $C_{1-6}$ alcohols, $C_{2-20}$ glycols, $C_{2-20}$ monoglycol ethers. The metal of the metal alkoxide can be potassium or sodium.

The methanol solvent system can include a co-solvent selected from the group consisting of glymes, glycols, monoglycol ethers, amino solvents, other oxygenated solvents and mixtures thereof. The co-solvent incorporated in the methanol solvent system can be, for example, triglyme, tetrahydrofuran, dioxane, polyethylene glycol, derivatives of polyethylene glycol or mixtures thereof.

The catalyst of the present invention can further include a co-catalyst, which is a metal selected from metals of Group 6, Group 7, Group 9 or mixtures thereof. More specifically, the co-catalyst can be a metal selected from the group consisting of Cr, Mo, W, Co, Ni, Fe, Cu, Ru, Rh, Pd, Pt and mixtures thereof. Preferably, the co-catalyst metal is selected from the group consisting of Cr, Mo, W, Co, Fe, Cu, Ru, Rh, Pd, Pt and mixtures thereof. The catalyst system can include the support for the catalyst which can be made of zeolites, clays, acidic zeolites, alumina, silica or mixtures thereof.

In another embodiment the catalyst of the present invention is a catalyst for the production of methanol from synthesis gas at low temperature and low pressure, the catalyst produced by reacting a transition metal complex having coordinating ligands selected from the group consisting of N-donor ligands, P-donor ligands, O-donor ligands, C-donor ligands, halogens and mixtures thereof or precursors thereof with an alkoxide in a methanol solvent system over a temperature range and pressure range over a period of time effective to form said catalyst, provided at least one C-donor ligand is not carbonyl. Whenever the transition metal complex includes coordinating ligands, wherein at least one C-donor ligand is not carbonyl, then the transition metal complex is non-toxic by comparison to nickel carbonyl.

The temperature range over which the catalyst can be used for the production of methanol from purified synthesis gas is from about room temperature to about 150° C. and the pressure range is from about 70 psig to 150 psig. And time ranges from about 1 minute to about 30 minutes.

In another aspect, the invention provides the method of producing methanol from purified synthesis gas comprising, said method comprises contacting at low temperature and low pressure synthesis gas with a homogenous catalyst dissolved in a methanol solvent system, the catalyst including a transition metal complex with coordinating ligands selected from the group consisting of N-donor ligands, P-donor ligands, O-donor ligands, C-donor ligands, halogens and mixtures thereof, wherein the transition metal complex is not transition metal carbonyl. The transition metal complex used in the catalyst for the method of producing methanol from synthesis gas has coordinating ligands preferably selected from the group consisting of chloride, acetylacetonate, 2,2-dipyridyl, bis (cyclooctadiene), 1,10-phenanthroline, 1,2-bis (diphenylphosphinoethane) and mixtures thereof. The useful temperature range for the temperature is from about 50° C. to about 150° C. and for the pressure is from about 70 psig to about 1500 psig. The alkoxide used in the method of the invention is a methoxide selected from the group consisting of potassium methoxide, sodium methoxide and mixtures thereof. The method of the present invention is conducted in a methanol solvent system which can be methanol or methanol and a co-solvent selected from the group consisting of tetrahydrofuran, p-dioxane, polyethylene glycol and derivatives of polyethylene glycol and mixtures thereof.

Whenever the synthesis gas comprises carbon dioxide, carbon monoxide and/or hydrogen it is preferable that in the method of the invention the homogenous catalyst also includes a co-catalyst metal which is selected from the metals of the groups consisting of Group 6, Group 7, Group 8, Group 9 and mixtures thereof. More specifically, the co-catalyst, can be a metal selected from the group consisting of Cr, Mo, W, Co, Ni, Fe, Cu, Ru, Rh, Pd. Pt and mixtures thereof. Preferably the co-catalyst is a metal selected from Cr, Mo, W, Co, Fe, Cu, Ru, Rh, Pd, Pt and mixtures thereof.

In another embodiment of the present invention provides a method for decomposition of a metal alkyl carbonate to carbon dioxide and the precursor metal of oxide comprising contacting the metal alkyl carbonate with a metal carbonyl dissolved in a methanol solvent system, wherein the metal is selected from metals of the groups consisting of Group 6, Group 7, Group 8, Group 9 and mixtures thereof.

As a result of the present invention a homogenous catalyst for the production of methanol from purified or non-purified synthesis gas is provided at low temperatures. The catalyst includes a transition metal capable of forming a transition metal complexes with coordinating ligands such that non-toxic catalysts which are not transition metal carbonyl are formed. The addition of a co-catalyst to the ligand bearing the transition metal enhances the ability of the homogenous catalyst to tolerate $CO_2$ present in non-purified synthesis gas.

Other improvements which the present invention provides over the prior art will be identified as a result of the following description which set forth the preferred embodiments of the present invention. The description is not in any way intended to limit the scope of the present invention, but rather only to provide the working example of the present preferred embodiments. The scope of the present invention will be pointed out in the appended claims.

DETAILED DESCRIPTION OF THE INVENTION

The instant invention relates to homogeneous catalyst formulations which can be used for the synthesis of methanol from synthesis gas including carbon monoxide, carbon dioxide and hydrogen. The homogeneous catalyst formulations provided by the present invention are non-toxic, easily prepared and exhibit superior activity when compared to conventional methanol catalysts, permitting the use of lower temperatures and pressures in the reactor and producing methanol at high gas conversion rates.

The homogeneous catalyst formulations of the present invention are comprised of two components dissolved in methanol or a methanol and co-solvent mixture. The two components are a transition metal complex having coordinating ligands and an alkoxide. The transition metal is selected from the group consisting of chromium, tungsten, osmium, rhodium, iridium, platinum, gold, zinc, copper, nickel, palladium, cobalt, ruthenium, iron, molybdenum, cadmium and mixtures of these metals. The preferred transition metals are nickel, palladium, molybdenum, copper, ruthenium, iron and mixtures thereof.

Coordinating ligands useful for complexing the transition metals of the homogenous catalyst formulations of the present invention include N-donor ligands, P-donor ligands, O-donor ligands, C-donor ligands, halogens or mixtures thereof. More specifically, examples of preferred coordinating ligands include without limitation chloride, acetylacetonate, 2,2'-dipyridyl (Bipy), bis (cyclooctadiene), 1,10-phenanthroline, 1,2-bis (diphenylphosphinoethane) and mixtures thereof. In certain embodiments the C-donor ligand includes CO, provided however, that at least one ligand of the transition metal complex is not carbonyl.

This two-component catalyst is in a solution of methanol, which is available from the methanol product in the reactor. A co-solvent may also be employed, preferably an organic oxygen containing co-solvent that is miscible with methanol. Suitable co-solvents include saturated hydrocarbons, amine based solvents, ethers, esters, alkyl polyethers and hydroxalkylpolyethers in which the carbon chain is interrupted by one or more oxy groups, and alcohols. The preferred co-solvents are tetrahydrofuran, 2-methyltetrahydrofuran, iso-octane, toluene, p-dioxane, t-amyl alcohol, t-butyl alcohol, polyalcohols, glycol derivatives such a polyethylene glycol and triglyme, the dimethyl ether of resorcinol, dimethyl oxalate, and crown ethers.

Because the homogeneous catalyst of the present invention possesses such high activity, the catalyzed production of methanol from carbon monoxide and hydrogen can be carried out under moderate conditions. The catalyst operates effectively at temperatures in the range of from about 20° C. to about 150° C., with temperatures in the range of from about 100° C. to about 150° C. being preferred. Likewise the pressure prevailing in the reactor can be as low as 50 psi and as high as 300 psi with the preferred pressure being in the range of from about 100 to about 150 psi.

The feed gas for the production of methanol using the present catalyst is synthesis gas. Synthesis gas can be generated either by steam reforming, partial oxidation with oxygen or air of natural gas or biomass. Preferably, synthesis gas is produced by the air partial oxidation of natural gas. This feed gas may be diluted with inert gases such as nitrogen and methane. The catalyst can tolerate minor quantities of hydrogen sulfide, carbon dioxide and water but it is preferred to use an approximately anhydrous, carbon dioxide-free synthesis gas.

The homogeneous catalyst of the present invention is the product of the reaction between the two materials used to prepare the catalyst, the non-toxic transition metal material and the alkoxide material. The transition metal material is a material capable of generating the corresponding non-toxic transition metal in methanol solution. As used herein "non-toxic" refers to materials that are nonvolatile and require minimum care during handling. More specifically, the transition metal complexes useful in the catalysts of the invention are non-toxic by comparison to nickel carbonyl.

The transition metal material may be the metal complex or a complex precursor thereof. As used herein, the term complex precursor means a material which, when dissolved in methanol, forms the transistion metal complex in situ. The transition metal complex or transition metal complex precursor may be used in the preparation of the instant catalyst in its mononuclear form or in cluster form.

The transition metal complex or complex precursor material may also be introduced into the methanol solution in which the homogeneous catalyst is to be prepared in the form of any supported species which will form, for instance, the complex salt, on its surface. In this way the homogeneous catalyst will be carried on a support, like zeolite, so that the system could function as either a homogeneous or heterogeneous catalyst. Other supports useful in the present invention are clays, acidic or basic supports such as natural and synthetic zeolites, alumina, silica, or carbon.

The second material used in the preparation of the homogeneous catalyst is the material that contributes the alkoxide component. Useful as this second reaction material is any metal, amine, or other material that will form or generate alkoxides in the presence of the methanol solvent system. Possible alkoxide generators are group IA, IIA and IIB metal alkoxides, where the alkoxy group is preferably derived from alcohols containing 1–6 carbon atoms. Preferred are the aliphatic alcoholates where the cation is an alkali or alkaline earth metal or a mixture thereof. Most preferred are the aliphatic alcoholates of sodium, potassium, rubidium, cesium, barium and calcium; with potassium methoxide most preferred. Examples of amines that will generate an alkoxide in a methanol solution are 1,8-diazobicyclo[5.4.0]undec-7-ene and tetramethylammonium methoxide.

In a preferred aspect of the present invention the homogenous catalyst system of the invention further comprise a co-catalyst thereby forming a hybrid catalyst system. It is well known in the art that the cause of deactivation of most catalysts containing alkoxide used in the manufacture of methanol from synthetic gas is primarily due to interaction of the alkoxide base with $CO_2$ to form PMC as was illustrated in reaction 2 above. It has been unexpectedly found that by incorporating a co-catalyst in the catalyst systems of the invention robust hybrid catalysts are obtained which can economically be used in the production of methanol from synthetic gas comprising many impurities including especially $CO_2$. The primary function of the co-catalyst is to reverse the reactions in which the alkoxide base is consumed to form PMC and/or a hydroxide base, thereby making the alkoxide base available for methanol synthesis. Metals useful as co-catalysts in the hybrid catalyst systems of the present invention include without limitation Cr, Mo, W, Co, Ni, Fe, Cu, Ru, Rh, Pd, Pt and mixtures thereof.

The proportions of the non-toxic transition metal complex and alkoxide components in the catalyst formulation will vary, depending upon whether methanol is used alone as the solvent or whether a co-solvent is used. Basically, the amount of metal and alkoxide in one liter of methanol containing solvent system varies from about 0.01 to about 2 moles of transition metal complex and from about 0.01 to about 20 moles of alkoxide. If methanol alone is the solvent, the preferred molar ratio is 1/100 while if tetrahydrofuran is used as a co-solvent, the preferred molar ratio is 1/0.5.

Batch methanol synthesis rates as high as 300 psi/min have been achieved with the homogeneous catalysts of the present invention. The simplicity of this active catalyst lies in the fact that the product (methanol) serves as the solvent and the alkoxide component can be derived from the product making the system mechanistically simple and economically attractive. The product methanol can be removed from the reaction zone together with non-reacted CO and $H_2$ as a gas simultaneously with its formation by the chemical reaction in the liquid phase. The catalyst is extremely selective for methanol synthesis. Conversions to methanol of as high as 94% are consistently achieved. The rate at which carbon monoxide and hydrogen react can be increased by carrying out the reaction in the presence of a co-solvent. Particularly recommended are THF, 2 methyl-THF, p-dioxane, t-amyl alcohol, t-butyl alcohol, triglyme and the polyethylene glycols, known as PEG-200, PEG-400 and PEG-600. The above co-solvents are preferably applied in molar or almost molar proportions with respect to methanol. If desired, however, also larger or smaller quantities may be chosen.

Since the reaction between CO and $H_2$ to form methanol catalyzed by the homogeneous catalyst of the present invention occurs in a liquid reaction phase, the feed gas can be supplied to the catalyst for contacting in any reactor that is designed for liquid phase/gas system operation. Likewise, the methanol production can be carried out in a reactor system designed for batch, semi-continuous or continuous production.

It is preferred to carry out the production of methanol using the instant catalyst using a reactor that is characterized by good mixture of the gas/liquid phases. The methanol product is removed from the reactor by bubbling an excess of carbon monoxide and hydrogen, or an inert carrier gas such as nitrogen, through the reactor. By removing methanol as a gas, the technical advantages to the production process associated with the catalyst, its activity, lifetime and handling are achieved. Alternatively, methanol can be removed in the liquid phase so that dissolved catalyst is carried with product flow from the reactor. Products are flashed in a separation zone and recovered catalyst is recirculated to the reactor.

The combination of low operating temperature needed by the instant catalyst and its high catalytic activity at very short contact times makes it possible to achieve very high conversion rates of the feed gas in the methanol synthesis. Equilibrium conversion of synthetic gas having 2 mols of hydrogen per mol of carbon monoxide at 100° C. and 150 psi has consistently been calculated to be about 94%. Furthermore, the liquid nature of the catalyst systems makes it possible to decouple gas liquid contacting for fast reaction from the removal of heat resulting from the exothermic reaction of CO and $H_2$ from the reactor. This decoupling can be done, for example, by circulating the catalyst through an external cooler or incorporating an inert low-boiling compound into the catalyst system which can be condensed externally and recycled to the reactor. The combination of the high thermodynamic equilibria of the process and the ability to decouple kinetics and heat transfer overcomes reactor design limitations imposed by current catalyst technology.

In one embodiment of the present invention, the homogeneous catalyst is prepared in situ in the reactor by adding the transition metal complex and the alkoxide to a solution of methanol and desired co-solvents, activators, etc. Methanol production can proceed immediately upon catalyst preparation. In an alternative approach, the homogeneous catalyst can be prepared separately in advance and loaded into the reactor when needed.

In one embodiment for methanol synthesis using the liquid phase catalyst of the present invention, feed synthesis gas enters the reactor which operates at 110° C. and 150 psi. Gas rises through the catalyst solution and forms methanol releasing heat which is removed, for example, by circulation of a coolant through coils in the reactor. Though this cooling system does not completely decouple cooling from reaction interface conditions, heat transfer to the coils is rapid and the reaction proceeds essentially isothermally at a favorable temperature because of the vigorous agitation and turbulence of the liquid induced by gas flow. As a result, conversion of 90% of the carbon monoxide can be achieved. The tail gas is, therefore, very small in volume and the cooler, separator and recycle compressor for recycling unconverted gas are very small in comparison to the requirements of similar components used with conventional heterogeneous catalysis. The small volume of gas may be insufficient to carry all the methanol overhead as vapor. In such a case, it is necessary to extract liquid from the reaction. This liquid is blended with condensate from the separator and constitutes the crude methanol which flows from the separation system. When liquid is removed from the reactor, the first distillation tower separates volatile catalyst components and returns them to the reactor. The second distillation tower produces methanol product as distillate. If this approach is taken to the production of methanol, and a co-solvent is to be used in the system, a co-solvent will be chosen that has a boiling point higher than methanol so that the methanol and co-solvent are separated in the second distillation tower and the col-solvent is returned as a liquid to the reactor.

EXAMPLES

The examples below further illustrate the various features of the invention and are not intended in any way to limit the scope of the invention which is defined in the appended claims. All materials used in the examples set forth below are commercially readily available or have been synthesized as described in each example. In all examples reciting time intervals, the times actually lapsed commence from the start of the change in pressure at room temperature. Except for comparative examples 1 and 2, the following examples describe non-$Ni(CO)_4$ systems. Specifically, the examples describe synthesis of nitrogen (N)-donor and phosphorous (P)-donor complexes of Ni and their comparative performance as methanol synthesis catalysts. Examples 24–26 are directed to a hybrid catalyst using $Fe(CO)_5$ as co-catalyst.

Example 1—Comparative Example

This example illustrates a methanol synthesis wherein the catalyst system is $Ni(CO)_4/KOCH_3$. The experiment was carried out in an AE (Autoclave Engineers) batch unit that consisted of a 0.55 L pressure vessel that was fitted with a Dispersimax® stirrer for efficient gas/liquid mixing. In this run, $KOCH_3$ (0.12 mol) was weighed inside a Labconoco glove box and dissolved in a 10% methanol/90% triglyme (volume/volume) solvent mixture (120 mL) to yield a light yellow homogeneous solution. The solution was poured into the pressure vessel and the vessel was quickly sealed and purged several times with $N_2$. $Ni(CO)_4$ (6 mmol) was added into the base solution through an injection port and the vessel was pressurized with 700 psig of 66% $H_2$/34% CO composition. A gas sample was then taken to establish the initial gas composition of the vessel. The automatic temperature controller and the stirrer were set at 120° C. and 1600 rpm respectively. The stirring speed of 1600 rpm ensured that the reaction was operating out of the mass transfer regime. The vessel contents were then stirred for 15 minutes at room temperature during which time the vessel pressure decreased from 700 to 671 psig due to gas dissolution and absorption by the base. At this time, methanol synthesis was initiated by heating the solution. The pressure continued to drop during heating and it was recorded at 297 psig at 120° C. After the pressure dropped to 230 psig, the reaction was quenched by replacing the heater with an ice-water bath. Once the vessel cooled to room temperature, the recorded final pressure was 102 psig. The average gas consumption rate was 54 mmol/min. Gas and liquid samples were taken for analysis and the final liquid volume was measured. During the second charge, the vessel was pressurized from 102 to 740 psig and the heating/cooling process was repeated. The final pressure was 91 psig at room temperature and the average gas consumption rate was 32 mmol/min during charge 2. A total of 1.488 mol syngas was consumed during the two charges.

The final gas composition was as follows: $H_2$=86.5%, CO=4.5%. The infrared (IR) of the gas phase of the pressure vessel showed the presence of CO (2160, 2100 cm$^{-1}$), a sharp band at 2040 cm$^{-1}$ for Ni(CO)$_4$ and a broad band at 1750 cm$^{-1}$ for methyl formate (MF). The final volume of the yellow solution was 140 mL resulting in a net increase of 20 mL during the run. The product selectivity was as follows: CH$_3$OH=99.1%, MF=0.9%, Dimethyl ether (DME)~trace. This run established the versatility of the reference Ni(CO)$_4$ catalyst system.

Example 2—Comparative Example

This example illustrates the effect of the nature of the co-solvent during methanol synthesis with the Ni(CO)$_4$/KOCH$_3$ reference catalyst system. In this run, triglyme was replaced with an equal volume of tetrahydrofuran (THF) while keeping the operating procedure the same as that described in Example 1. The initial 750 psig syngas pressure decreased to 690 psig on stirring at room temperature. On heating the vessel, the pressure decreased to 630 psig at 50° C. in 3 minutes, maximized to 679 psig at 80° C. in 7 minutes and then decreased to 443 psig at 120° C. in 11.3 minutes. The pressure decreased to 211 psig under isothermal operation (at 120° C.) in 15.5 minutes. The average gas consumption rate was 66 mmol/min. On cooling to room temperature, the final pressure was 78 psig. During charge 2, the vessel was repressurized to 770 psig (from 78 psig) at room temperature and decreased to 703 psig on stirring. The pressure increased to 714 psig at 72° C. at 9.5 minutes, decreased to 545 psig at 120° C. at 13.5 minutes and then isothermally decreased to 250 psig at 20.3 minutes. The final room temperature pressure was 114 psig. The average gas consumption rate was 46 mmol/min.

After two charges, the gas analysis yielded: H$_2$=83.3%, CO=8.6%. A total of 1.504 mol syngas was consumed. The final yellow solution showed a net increase of 19.2 mL increase in volume and analyzed to yield the following product selectivity: CH$_3$OH=95.7%, MF=4.0%, DME=0.3%. In comparison with Example 1, the reaction rate was higher in THF. The signature peak at 2040 cm$^{-1}$ for Ni(CO)$_4$ in the gas-phase IR spectrum established that free Ni(CO)$_4$ was present in the pressure vessel during this run.

Example 3

In this example NiCl$_2$ was used as a replacement for toxic Ni(CO)$_4$. The chloride salt of Ni$^{2+}$ is stable in air, inexpensive and non-toxic. The catalytic activities of NiCl$_2$ and Ni(CO)$_4$ were compared. The hydrated salt NiCl$_2$.6H$_2$O was dried overnight in vacuo at 110° C. to yield anhydrous NiCl$_2$. In this run, Ni(CO)$_4$ as used in Example 1, was replaced with an equimolar quantity of yellow anhydrous NiCl$_2$. The run of Example 1 was repeated except that the catalyst loading procedure of Example 1 was somewhat modified in that KOCH$_3$, NiCl$_2$ and the solvent mixture were loaded together in the vessel. The pressure decreased from 748 to 715 psig on stirring at room temperature. The pressure maximized at 795 psig at 72° C. in 10 minutes and then decreased to 521 psig at 120° C. in 14.6 minutes from the time the pressure was decreased at room temperature. The pressure dropped to 212 psig under isothermal operation (at 120° C.) in 19.5 minutes. On cooling to room temperature, the final pressure was 92 psig. The average gas consumption rate was 98 mmol/min. For charge 2, the vessel was repressurized to 740 psig from 92 psig that decreased to 717 psig on stirring. The pressure maximized at 763 psig at 83° C. in 10.5 minutes, decreased to 470 psig at 120° C. in 16 minutes, then further decreased to 254 psig in 21.3 minutes from the start of the reaction at room temperature. The final pressure was 105 psig at room temperature. The average gas consumption rate was 47 mmol/min during charge 2.

The gas analysis was as follows: H$_2$=86.6%, CO=3.0%. A total of 1.549 mol syngas was consumed during the two charges. The volume of the final yellow solution indicated a net increase of 20.7 mL. The product selectivity was: CH$_3$OH=99.2%, MF=0.2%, DME=0.6%. The IR spectrum of the vessel gas phase indicated the presence of Ni(CO)$_4$ at 2040 cm$^{-1}$ though the peak intensity was about 50% of that observed in Example 1. This example demonstrates that: 1) NiCl$_2$ is more efficient catalyst than Ni(CO)$_4$, 2) the concentration of free Ni(CO)$_4$ in the vessel is decreased by 50% when storing with NiCl$_2$. Thus, the presence of chloride ions inhibits Ni(CO)$_4$ formation during methanol synthesis.

Example 4

This example shows that the alkoxide base is necessary to catalyze methanol synthesis with NiCl$_2$. The experiment in Example 3 was repeated except no KOCH$_3$ was added to the pressure vessel. The initial 717 psig pressure at room temperature was maximized at 957 psig at 120° C. and remained constant for one hour. The 715 psig final pressure was virtually unchanged from the initial pressure of 717 psig.

The final gas analysis was: H$_2$=66.0 6%, CO 34.0%. The volume of the solution was unchanged. The IR spectrum of the vessel gas phase identified a sharp Ni(CO)$_4$ band at 2040 cm$^{-1}$. A comparison with the IR spectrum in Example 1 showed that the intensity of the Ni(CO)$_4$ peak in this experiment was about 20% of that observed with Ni(CO)$_4$ in Example 1. No net methanol was produced in this experiment indicating that NiCl$_2$ without KOCH$_3$ was not effective for methanol synthesis.

Example 5

This example illustrates the use of nickel (2+) acetylacetonate (Ni(acac)$_2$) as a replacement for Ni(CO)$_4$. The experiment of Example 3 was repeated after replacing NiCl$_2$ with an equimolar amount of Ni(acac)$_2$. The initial 738 psig pressure decreased to 698 psig on stirring. On heating, the pressure further decreased to 676 psig, then maximized at 750 psig at 60° C. in 10 minutes and then kept decreasing until 184 psig at 115° C. in 17 minutes from the start of the heating step at room temperature. The average gas consumption rate was 72 mmol/min. On cooling to room temperature, the final pressure was 78 psig. For charge 2, the vessel was repressurized with syngas to 732 psig (from 78 psig) that decreased to 705 psig on stirring. On heating, the pressure decreased to 697 psig at 52° C. in 8 minutes and continued to decrease to 328 psig at 115° C. in 17.5 minutes from the start of the heating step. The final pressure at room temperature was 173 psig. The average gas consumption rate was 47 mmol/min during charge 2.

The gas analysis was: H$_2$=87.4%, CO=7.0%. A total of 1.463 mol syngas was consumed. The final amber solution volume indicated a net increase of 20 mL. The product selectivity was as follows: CH$_3$OH=98.0%, MF=1.4%, DME=0.6%. A sharp IR band at 2040 cm$^{-1}$ in the gas-phase spectrum was identified as Ni(CO)$_4$. The band intensity was about 80% of that observed for the reference Ni(CO)$_4$/KOCH$_3$ system in Example 1. Ni(acac)$_2$ showed superior performance as compared to Ni(CO)$_4$ in terms of reaction rate as well as decreased Ni(CO)$_4$ concentration.

Example 6

This example describes the synthesis and evaluation of a nitrogen (N)-donor complex of Ni as catalyst material for methanol synthesis. The N-donor ligand used was 2,2'-dipyridyl (Bipy). First, the Ni-Bipy-CO complex was synthesized. A colorless solution formed on adding Bipy (6 mmol) to a degassed solution of n-hexane (50 mL) under argon. A brick red solid precipitated on slowly adding $Ni(CO)_4$ (5 mmol) to the Bipy solution (Bipy/Ni=1/1 mole ratio) with concomitant CO evolution that ceased in a few minutes. The slurry was refluxed for one hour under argon, cooled to room temperature, filtered and washed twice with hexanes in the glove box. The brick red crystalline solid was dried in vacuo for two hours. The product yield was 93% based on Ni content. Spectroscopic data: IR (KBr disc) bands at 2030, 1980, 1885 $cm^{-1}$; Ultraviolet/Visible (UV/VIS) absorption bands in triglyme solvent: 490 and 377 nm. The characterization established that the brick red product contained both CO and Bipy ligands with Ni/Bipy ratio of 1/1.

The brick red Ni-Bipy-CO complex was evaluated for methanol synthesis. The run in Example 3 was repeated except that $NiCl_2$ was replaced with an equimolar Ni-Bipy-CO complex. The initial syngas pressure decreased from 742 to 703 psig on stirring at room temperature. On heating the pressure decreased to 659 psig, maximized at 670 psig at 48° C. in 7.5 minutes and then decreased to 220 psig at 120° C. in 17 minutes then cooled at 108 psig to room temperature. The average gas consumption rate was 56 mmol/min. For charge 2, the vessel was repressurized with syngas to 800 psig from 108 psig that maximized at 777 psig at 97° C. and then decreased to 281 psig at 120° C. in 22 minutes from the start of the repressurizing step. The final pressure at room temperature was 150 psig. The average gas consumption rate was 48 mmol/min during charge 2.

The final gas analysis was: $H_2$=81.7%, CO=11.2%. A total of 1.500 mol syngas was consumed during the run. The final amber solution was homogeneous and a net volume increase of 21 mL was calculated. Product selectivity: $CH_3OH$= 95.2%, MF=3.3%, DME=1.5%. The gas phase IR spectrum showed a sharp band at 2040 $cm^{-1}$ for $Ni(CO)_4$ and a broad band at 1750 $cm^{-1}$ for MF. The $Ni(CO)_4$ peak was somewhat smaller than that observed in Example 1.

Example 7

This example shows that non-$Ni(CO)_4$ complexes can be substituted to synthesize ligated Ni complexes as catalysts for methanol synthesis from synthetic gas. In this example, bis(cyclooctadiene) nickel(0) complex ($Ni(COD)_2$) was substituted for $Ni(CO)_4$ to form a Ni-Bipy complex. $NiCl_2$ in Example 3 was replaced with an equimolar quantity of $Ni(COD)_2$ and Bipy each (Ni/Bipy=1/1 mole ratio) to allow in situ formation of a Ni-Bipy complex. The initial 743 psig syngas pressure decreased to 703 psig on stirring at room temperature. The vessel took 22 minutes to heat to 120° C. during which time the pressure maximized to 809 psig at 100° C. in 15 minutes. The vessel was cooled when the pressure decreased to 335 psig in 44 minutes with final pressure of 185 psig at room temperature. The average gas consumption rate was 20 mmol/min.

The final gas analysis was: $H_2$=85.4%, CO=8.1%. A total of 714 mmol syngas was consumed during the run. The final deep red solution volume indicated a net increase of 12 mL.

The product selectivity was: $CH_3OH$=96.8%, MF=2.8%, DME=0.4%. Gas phase IR data: $Ni(CO)_4$ at 2040 $cm^{-1}$ and MF at 1750 $cm^{-1}$. In comparison to the data in Example 1, two observations were: 1) the $Ni(CO)_4$ peak was about 50% smaller and 2) the reaction rate was 2.7 times slower than with the $Ni(COD)_2$/Bipy/$KOCH_3$ system.

Example 8

In this example, the synthesis procedure for making the Ni-Bipy-CO complex as described in Example 6 was followed. Specifically, Example 6 was repeated with the Ni-Bipy-CO complex in which the starting $Ni(CO)_4$/Bipy ratio was 1:1. A brick red complex was isolated that was identical to that obtained with the $Ni(CO)_4$/Bipy ratio of 1:1. This was further confirmed when 1 mole of unreacted Bipy was isolated from the filtrate of the present example. The spectroscopic data further confirmed that starting with $Ni(CO)_4$/Bipy ratio of 1:1 and 1:2 both yielded the identical brick red Ni-Bipy-CO complex that contained Ni/Bipy mole ratio of 1:1.

The brick red complex was evaluated for methanol synthesis under conditions of Example 3. The run data was essentially identical to that reported in Example 6.

Example 9

This example shows that methanol synthesis can be facilitated by N-donor bidentate ligands other than Bipy. In this run, 1,10-phenanthroline (Phen) was utilized. The synthesis procedure described in Example 6 for Bipy was followed. The 95% hexane/5% ethanol solvent mixture replaced pure hexane solvent due to limited solubility of Phen in pure hexane. A red solid was isolated in 93% yield (based on 10 mmol of $Ni(CO)_4$ starting material). Spectroscopic data: IR (KBr disc): 1970 and 1865 $cm^{-1}$; UV/VIS data: $\lambda_{max}$=476 nm in methanol. The Phen complex was assigned the $Ni(Phen)(CO)_2$ formulation.

For comparative activity, the Ni-Bipy complex in Example 6 was replaced with an equimolar Ni-Phen-CO complex. On pressurizing the vessel at 750 psig and subsequent heating to 120° C., the final pressure decreased to 105 psig at room temperature. A total of 774 mmol syngas was consumed. The average gas consumption rate was 44 mmol/min. The final red solution volume indicated a net increase of 10 mL. The product selectivity was: $CH_3OH$=97.0%, MF=2.4%, DME=0.6%. The IR spectrum of the final gas phase indicated the presence of $Ni(CO)_4$ that was 20% of that noted for the $Ni(CO)_4$/$KOCH_3$ reference system in Example 1.

Example 10

This example evaluates the performance of a Ni complex containing a monodentate phosphorous (P)-donor ligand. A green solid formed on adding $Ni(CO)_4$ to a refluxing solution of triphenylphosphine ($PPh_3$) in a 1:1 mole ratio in hexane. After filtration, and air-drying, the yield was 62% (based on 10 mmol $Ni(CO)_4$). IR data (KBr disc): 2060 and 1990 $cm^{-1}$. The green solid was formulated as $Ni(PPh_3)(CO)_3$.

Under methanol synthesis conditions of Example 6, the initial syngas charge at 750 psig was recovered unreacted after heating at 120° C. for one hour. The run data showed that no methanol was synthesized and no $Ni(CO)_4$ was detected in the gas phase.

Example 11

In this example, the procedure for methanol synthesis described in Example 10 was repeated with $Ni(CO)_4$/$PPh_3$ in a 1:2 mole ratio. A cream colored solid was isolated in 89% yield based on 10 mmol $Ni(CO)_4$. IR data (KBr disc): 1990 and 1930 $cm^{-1}$. The cream colored complex was formulated as $Ni(PPh_3)_2(CO)_2$.

As in Example 10, the unreacted syngas was recovered after heating this complex under methanol synthesis conditions of Example 6 at 120° C. for one hour. The results of this example showed that no methanol was synthesized and no Ni(CO)$_4$ was detected in the gas phase.

Example 12

In this example the procedure for methanol synthesis described in Example 11 was followed except that the mole ratio of Ni(CO)$_4$/PPh$_3$ was changed to 1:4. A cream colored complex was isolated that was identical to that synthesized in Example 11. Under methanol synthesis conditions of Example 10, the Ni(PPh$_3$)$_2$(CO)$_2$ complex was virtually inactive when heated under 750 psig syngas at 120° C. for one hour.

Example 13

This example describes methanol synthesis activity of a bidentate phosphine-nickel complex. Replacing PPh$_3$ with 1,2-bis(diphenylphosphino)ethane (Diphos) in Example 10 with Ni/Diphos mole ratio of 1:1 in 95% hexane/5% ethanol solvent, a pale yellow solid was isolated in 85% yield. IR data (KBr) disc: 1990, 1940 cm$^{-1}$. The bidentate ligand forces a cis geometry in the synthesized complex Ni(Diphos)(CO)$_2$.

As in Example 10, the Ni-Diphos complex was heated under 700 psig syngas at 120° C. for one hour. The complex was inactive for methanol synthesis under these conditions.

Selective data from Examples 1–13 are summarized in Table 1. The results summarized in Table 1 show that Ni complexes with N-donor ligands can be readily synthesized or generated in situ by adding equimolar Ni(CO)$_4$ and the ligand to the vessel. Ni-ligand complexes were conveniently substituted for the toxic Ni(CO)$_4$ to catalyst methanol synthesis from synthesis gas.

TABLE 1

Catalytic activity of various Ni complexes for methanol synthesis

| Run | Catalyst | Rate, mmol/min | MeOH[a] | MF[b] | DME[c] |
|---|---|---|---|---|---|
| 1 | Ni(CO)$_4$ | 54 | 99.1 | 0.9 | Trace |
| 2 | Ni(CO)$_4$ | 66 | 95.7 | 4.0 | 0.3 |
| 3 | NiCl$_2$ | 98 | 99.2 | 0.2 | 0.6 |
| 4 | NiCl$_2$ | — | — | — | — |
| 5 | Ni(acac)$_2$ | 72 | 98 | 1.4 | 0.6 |
| 6 | Ni(CO)$_4$/Bipy (1/1) | 56 | 95.2 | 3.3 | 1.5 |
| 7 | Ni(COD)$_2$/Bipy (1/1) | 20 | 96.8 | 2.8 | 0.4 |
| 9 | Ni(CO)$_4$/Phen (1/1) | 44 | >97 | 2.4 | <0.6 |
| 10 | Ni(PPh$_3$)(CO)$_3$ | — | No activity | | |
| 11 | Ni(PPh$_3$)$_2$(CO)$_2$ | — | No activity | | |
| 12 | Ni(PPh$_3$)$_2$(CO)$_2$ | — | No activity | | |
| 13 | Ni(diphos)(CO)$_2$ | — | Trace | | |

[a] MeOH is methanol
[b] MF is methylformate
[c] DME is dimethylether

The following examples 14 to 17 show that the Ni-N-donor complexes could also operate at a lower concentration of the alkoxide base.

Example 14

In this example, the procedure described in Example 1 was followed under carefully chosen operating conditions. The operating conditions in the 0.55 L AE batch unit were as follows: 120 mL solvent, 6 mmol Ni complex, syngas: 66% H$_2$/34% CO; the initial pressure was approximately 750 psig at room temperature, and the temperature controller was set at 120° C. In this run, the Ni-Bipy-CO complex was generated in situ by adding 0.12 mol KOCH$_3$, 12 mmol Bipy (Bipy/Ni mole ratio was 2:1) and 120 mL 10% MeOH/90% triglyme (volume/volume) solvent mixture. 6 mmol Ni(CO)$_4$ was added after the pressure vessel was sealed. The vessel was pressurized with 768 psig syngas mixture, then the pressure of the mixture decreased to 703 psig on stirring. On heating, the pressure of the mixture decreased further to 621 psig at 35° C. at 5 minutes, maximized to 639 psig at 60° C. at 8 minutes and then decreased to 173 psig at 120° C. at 18 minutes. The final pressure was 60 psig at room temperature. The average gas consumption rate was 62 mmol/min. For charge 2, the vessel was repressurized with syngas to 803 psig (from 60 psig) then the pressure was dropped to 760 psig on stirring. On heating, the pressure maximized at 768 psig at 35° C. and then the pressure decreased to 304 psig at 120° C. at 19 minutes and further to 209 psig at 23 minutes from the start of the heating step. The final pressure was 87 psig at room temperature. The average gas consumption rate was 37 mmol/min during charge 2.

The final gas analysis was: H$_2$=78.9%, CO=11.2%. A total of 1.423 mol syngas was consumed during the run of this example. The final red solution volume indicated a net volume increase of 29 mL. Product selectivity: CH$_3$OH= 98.8%, MF=1.0%, DME=0.2%.

Example 15

This example shows that even with increased basicity caused by the presence of the Bipy ligand, the presence of KOCH$_3$ is necessary to affect methanol synthesis. The procedure of example 14 was repeated except that the solvent was changed to 100% triglyme and no KOCH$_3$ was added. At Ni/Bipy ratio of 1:4, only 3 psi syngas was consumed at 120° C. in 29 minutes when the vessel was charged with 750 psig syngas. A small amount of Ni(CO)$_4$ was detected in the gas phase.

Example 16

In this example the operating conditions were kept the same as those described in Example 14 except that the Ni/Bipy ratio was 1:4 and KOCH$_3$ was decreased to 30 mmol. The initial 768 psig syngas pressure decreased to 717 psig on stirring. During heating from room temperature to 120° C., the pressure maximized to 769 psig at 89° C. in 14 minutes and decreased to 309 psig in 30 minutes. The final pressure was 146 psig at room temperature. The average gas consumption arte was 55 mmol/min. A total of 1.106 mol syngas was consumed. The final totally homogeneous amber solution indicated a net volume increase of 19 mL.

The final gas analysis was: H$_2$=67.6%, CO=30.3%. Product selectivity: CH$_3$OH=89.5%, MF 9.3%, DME=1.2%. A higher yield of MF was noted. The data confirmed that even at 25% of the base concentration used in this run, only a slight decrease in the reaction rate was observed.

Example 17

In this example, the KOCH$_3$ concentration was further decreased to 24 mmol and the Ni/Bipy ratio was 1:4. The operating conditions were kept the same as in Example 14. The vessel was pressurized at 768 psig of initial syngas pressure then decreased to 704 psig on stirring. During heating from room temperature to 120° C., the pressure maximized to 753 psig at 81° C. in 14 minutes and then decreased to 270 psig in 30 minutes at 120° C. The final pressure was 145 psig at room temperature. The average gas consumption rate was 36 mmol/min. A total of 752 mmol syngas was consumed. The final volume increase was 9 mL.

The final gas analysis: $H_2$=69.8%, CO=28.0%. Product selectivity: $CH_3OH$=92.2%, MF=7.0%, DME=0.8%. A higher yield of MF was noted.

The results obtained in Examples 14–17 are summarized in Table 2 below. The results of the original $Ni(CO)_4$/$KOCH_3$ and the new Ni-Bipy-CO/$KOCH_3$ catalyst systems are compared in Table 3 below. It is apparent that the new catalyst formulations are superior to the original system with respect to: 1) non-toxicity of the Ni-Bipy-CO catalyst component, 2) higher rates of reaction up to 12 G-mol $CH_3OH$/L catalyst/hour while the system maintains a high methanol selectivity of 98% or higher. These tables illustrate the superior performance of methanol synthesis catalyst formulations preferably based on complexes of Ni and other transition metals with coordinating ligands selected from N-donor, P-donor, O-donor, halogens or mixtures thereof that eliminate handling of toxic $Ni(CO)_4$ during catalyst loading and potentially require lower concentration of $KOCH_3$ while maintaining high reaction rates and methanol product selectivity.

TABLE 2

Catalytic activity of Ni—N-donor complexes for methanol synthesis
0.5L AE Zipperclave batch reactor, Solvent = 120 mL, [Ni-Bipy-CO] = 0.05 M, Syngas: 66% $H_2$/34% CO, T = 120° C., $P_1$ = 700 psig.

| | % Solvent | | | KOMe[b] | Bipy | Rate | % Product Selectivity | |
|---|---|---|---|---|---|---|---|---|
| Run | Triglyme | MeOH[a] | $H_2O$ | M | M | Mmol/min | MeOH | MF[c] |
| 14 | 90 | 10 | — | 1.0 | 0.10 | 62 | 98.8 | 1.0 |
| 15 | 100 | — | — | — | 0.20 | — | — | — |
| 16 | 90 | 10 | — | 0.25 | 0.20 | 55 | 89.5 | 9.3 |
| 17 | 90 | 10 | — | 0.20 | 0.20 | 36 | 92.2 | 7.0 |

[a]MeOH is methanol
[b]KOMe is $KOCH_3$
[c]MF is methylformate
[d]DME is dimethylether

TABLE 3

Data comparison: Original vs. Modified Catalyst
Solvent: Triglyme/MeOH; Catalyst = 0.05M

| Catalyst | Solvent ratio[a] | Gas $P_T$, psig | $N_2$ | Base M | T, ° C. | % CO Conversion | Rate G-mol MeOH/L.h | MeOH selectivity |
|---|---|---|---|---|---|---|---|---|
| $Ni(CO)_4$ | 90/10 | 600[b] | 5% | 1.0 | 130 | >91 | 8.9 | 92.3 |
| $Ni(acac)_2$ | 85/15 | 300[b] | 7% | 1.0 | 130 | >99 | 1.1 | 89.4 |
| Ni-Bipy-CO | 90/10 | 500 | — | 1.0 | 120 | >90 | 12 | 98 |
| Ni-Bipy-CO | 90/10 | 500 | — | 0.25 | 120 | >90 | 8.8 | 89.5 |

[a]triglyme/methanol
[b]syngas contained $N_2$

The following examples illustrate that a facile decomposition of PMC can yield the original $KOCH_3$ with an evolution of $CO_2$. Furthermore, $CO_2$ can be subsequently processed via the water-gas-shift (WGS) reaction to yield CO for conversion to methanol.

$$H_2+CO_2 \rightarrow CO+H_2O \qquad [4]$$

The overall reaction, in essence, allows processing of $CO_2$ to methanol. Such a system forms the basis for a hybrid catalyst system. The following examples illustrate that PMC, which is formed by the interaction of the alkoxide base with $CO_2$, can be readily prepared and then decomposed to yield $KOCH_3$. For the experiments conducted in Examples 18 and 26, PMC was synthesized according to the following procedure. 50 grams of $KOCH_3$ was dissolved in 50% methanol/50% p-dioxane (volume/volume) solvent mixture under $N_2$. A white solid precipitated on bubbling $CO_2$ through the resulting solution at ambient temperature. The bubbling of $CO_2$ was continued until no more solid precipitated. The white PMC was filtered, washed with p-dioxane and dried in vacuo. Yield: 75 grams or 92% (mole/mole basis). The hygroscopic crystalline white solid was stored in a dry glove box. The solid PMC was used in the following examples to demonstrate that Reaction [2] above could be reversed to yield the original $KOCH_3$.

Examples 18

In this example, the thermal decomposition of PMC was measured. A customized AE Zipperclave batch unit was used in this study. The batch unit consisted of a 0.550 L vessel and fitted with a Dispersimaxo® for back mixing during stirring. The batch unit had ports for: 1) gas inlet and outlet and 2) liquid inlet and outlet. The run procedure involved addition of 10 mmol PMC and 125 mL MeOH solvent. The vessel was purged with $N_2$, pressurized at 300 psi with syngas of the composition 66% $H_2$/34% CO and heated to 140° C. The $CO_2$ evolution was followed as a function of time by analyzing the vessel gas-phase on a gas chromatograph ("GC") fitted with a molecular sieve 13X (10'×⅛") column with He as the carrier gas. The mole % PMC decomposition was calculated as follows:

$$\text{Mole \% PMC decomposition} = \frac{\text{Moles CO}_2 \text{ measured}}{\text{Initial moles of PMC}}$$

The decomposition was 80% at 50 minutes and maximized to 90% at 105 minutes form the start of the run. The final solution was homogeneous because KOMe is soluble in methanol. The data indicated that the endothermic PMC decomposition reaction proceeded slowly at 140° C. as compared to the Ni-catalyzed methanol synthesis reaction that is usually complete in less than 30 minutes.

Examples 19

In this example the procedure of example 18 was repeated by replacing methanol with poly-(tetrahydrofuran)-250. The PMC decomposition was measured at 80% in 60 minutes and maximized to 90% at 140° C. in 150 minutes from the start of the run. These results showed that poly (tetrahydrofuran)-250 was a poor solvent for PMC decomposition as compared to methanol.

Examples 20

In this example the procedure of example 18 was repeated, however, 100% methanol was replaced with 20% methanol/80% Polyethyleneglycol (PEG)-400 solvent. A complete decomposition of PMC was measured at 140° C. in 150 minutes from the start of the run. The final yellow solution was homogeneous.

Examples 21

In this run, the procedure of example 18 was again repeated, however, 100% methanol solvent was replaced with 10% methanol/90% triglyme solvent mixture. The PMC decomposition was measured to be 60% in 40 minutes with complete decomposition in 140 minutes at 140° C.

Examples 22

This example illustrates that PMC was the only source of $CO_2$. The procedure of Example 21 was repeated with no added PMC. In one hour, about 1% $CO_2$ was detected.

Examples 18–21 illustrate that the decomposition of PMC to regenerate $KOCH_3$ is feasible by heating PMC at 140° C. However, the kinetics of the reaction were too slow to be compatible with the methanol synthesis reaction even at 140° C.

The following examples demonstrate the effect of added catalyst to speed up the PMC decomposition reaction.

Examples 23

This reference experiment was conducted to show that $KOCH_3$ did not produce $CO_2$ under the selected experiment conditions. The experiment in Example 18 was repeated by replacing; 1) 100% MeOH solvent with 10% methanol/90% triglyme solvent mixture and 2) PMC with 10 millimoles $KOCH_3$. On heating the solution under 300 psig syngas (66% $H_2$/34% CO) at 140° C. for 90 minutes, only 1.3 mmol $CO_2$ was measured. The final solution was clear yellow.

Examples 24

This experiment was conducted in the AE batch unit described in Example 18. PMC was weighed in the glove box. PMC was dissolved in 125 mL 10% methanol/90% triglyme solvent mixture, 5 millimoles $Fe(CO)_5$ was loaded in to the pressure vessel. The vessel was purged three times with $N_2$ (50 psig each time) and then pressurized with 300 psig syngas of the 66% $H_2$/34% CO ratio. The vessel was heated to 140° C. The gas-phase of the vessel was analyzed by GC. The measured mole % $CO_2$ values as a function of time were: 13 millimoles in 32 minutes; 17 millimoles in 60 minutes from the start of the pressurizing step. A comparison of the data obtained in this example with the results obtained in Example 21 showed that $CO_2$ was produced faster in the presence of $Fe(CO)_5$. These results demonstrate $Fe(CO)_5$ catalyzed the decomposition of PMC.

Examples 25

Example 24 was repeated with no added PMC. Thus, 5 millimoles $Fe(CO)_5$ in 10% methanol/90% triglyme solvent mixture (100 mL) under 300 psig syngas of the 66% $H_2$/34% CO ratio was heated at 140° C. After one hour, only a negligible amount (0.14 millimole) of $CO_2$ was measured by GC. These results demonstrated that: 1) $Fe(CO)_5$ was not the source of $CO_2$ and 2) the 10% methanol/90% triglyme solvent mixture was also not the source of $CO_2$. Thus, PMC was the only source of $CO_2$ in the run of Example 24.

Examples 26

This example shows that metals other than Fe are effective catalysts for the PMC decomposition reaction. In this run, under the conditions of Example 24, $Fe(CO)_5$ was replaced with 1.7 millimoles of $Ru_3(CO)_{12}$ (5 millimoles equivalent Ru). On heating to 140° C. as described in Example 24, the measured $CO_2$ indicated about 85% PMC decompostion in less than 5 minutes. After further heating under isothermal conditions, a total of 28 mmol $CO_2$ was measured in 20 minutes from the start of the heating cycle. This value held constant during heating for 120 minutes. These data indicated that $Ru_3(CO)_{12}$ was a superior catalyst than $Fe(CO)_5$ for PMC decomposition under the chosen reaction conditions.

Examples 1–26 support the scope of the present invention. In a preferred embodiment of the present invention the catalyst formulation system includes a complex of ligated to a Ni ligand selected from N-donor, O-donor, P-donor, halogens and mixtures thereof. A preferred catalyst formulation contains N-donor ligands such as 2,2'-dipyridyl. The Ni-Bipy-CO catalyst was very effective for methanol synthesis from syngas that is purified to remove $CO_2$ to ppm levels.

The addition of a co-catalyst such as $Fe(CO)_5$ to the ligand bearing Ni system enhances its ability to tolerate $CO_2$. The co-catalyst is selected from Group VIII metals with Ru as a preferred metal. The primary function of the co-catalyst is to reverse Reactions [2] and [3] to make the alkoxide base available for methanol synthesis. Such a system can operate in a solvent medium consisting of methanol solvent and a co-solvent such as glymes, glycols under mild conditions of temperature of less than 150° C. and pressure of less than 450 psig to efficiently produce methanol.

Thus, while we described what are the preferred embodiments of the present invention, further changes and modifications can be made by those skilled in the art without departing from the true spirit of the invention, and it is intended to include all such changes and modifications as come within the scope of the claims set forth below.

What is claimed is:

1. A homogeneous catalyst comprising a transition metal complex containing coordinating ligands, and a metal alkoxide, wherein said homogeneous catalyst is dissolved in a methanol solvent system and said homogeneous catalyst is capable of producing methanol from synthesis gas, provided said coordinating ligands are not all carbonyl, and the transition metal is selected from the group consisting of Cr, Mo, W, Fe, Ru, Os, Co, Rh, Ir, Ni, Pd, Pt, Au, Zn, or Cd, or a combination thereof.

2. The homogenous catalyst of claim 1, wherein said coordinating ligands are selected from the group consisting of N-donor ligands, P-donor ligands, O-donor ligands, C-containing ligands, halogens and mixtures thereof.

3. The homogenous catalyst of claim 1, wherein said transition metal complex and said alkoxide are completely dissolved in the methanol solvent system to yield a homogeneous solution.

4. The homogenous catalyst of claim 1, wherein said synthesis gas comprises CO and $H_2$.

5. The homogenous catalyst of claim 1, wherein said transition metal is selected from the group consisting of Ni, Pd, Mo, Ru, Fe and mixtures thereof.

6. The homogenous catalyst of claim 1, wherein said coordinating ligands are selected from the group consisting of chloride, acetylacetonate, 2,2-dipyridyl, bis (cyclooctadiene), 1,10-phenanthroline, 1,2-bis (diphenylphosphinoethane) and mixtures thereof.

7. The homogenous catalyst of claim 1, wherein the metal in said metal alkoxide is selected from alkali metals or alkaline earth metals.

8. The homogenous catalyst of claim 1, wherein the alkoxide in said metal alkoxide is derived from $C_{1-6}$ alcohols, $C_{2-20}$ glycols, $C_{2-20}$ monoglycol ethers.

9. The homogenous catalyst of claim 7, wherein said metal of said metal alkoxide is potassium or sodium.

10. The homogenous catalyst of claim 9, wherein said metal alkoxide is potassium methoxide or sodium methoxide.

11. The homogenous catalyst of claim 1, wherein said methanol solvent system is methanol.

12. The homogenous catalyst of claim 11, wherein said methanol solvent system further comprises a co-solvent selected from the group consisting of glymes, glycols, monoglycol ethers, amino solvents, other oxygenated solvents and mixtures thereof.

13. The homogenous catalyst of claim 12, wherein said co-solvent is selected from the group consisting of triglyme, tetrahydrofuran, dioxane, polyethylene glycol, derivatives of polyethylene glycol and mixtures thereof.

14. The homogenous catalyst of claim 1, further comprising a co-catalyst selected from the group consisting of Cr, Mo, W, Co, Ni, Fe, Ru, Rh, Pd, Pt and mixtures thereof.

15. A catalyst system comprising the catalyst of claim 1 further comprising a support therefor.

16. The catalyst system of claim 15, wherein said support is selected from the group consisting of zeolites, clays, acidic zeolites, alumina, silica and mixtures thereof.

17. The homogenous catalyst of claim 1, wherein said catalyst is capable of producing methanol from synthesis gas at a temperature of about room temperature to about 150° C. and at a pressure of about 1500 psig to about 70 psig.

18. The homogenous catalyst of claim 17, wherein said catalyst is capable of producing methanol from synthesis gas in a period of time of about one minute to about thirty minutes.

19. The homogeneous catalyst of claim 4, wherein said synthesis gas further comprises $CO_2$.

20. A homogeneous catalyst for the production of methanol from synthesis gas at low temperature and low pressure, said homogeneous catalyst produced by reacting a transition metal complex having coordinating ligands selected from the group consisting of N-donor ligands, P-donor ligands, O-donor ligands, C-donor ligands, halogens and mixtures thereof or precursors thereof with a metal alkoxide, wherein said homogeneous catalyst is dissolved in a methanol solvent system, provided said coordinating ligands are not all carbonyl, and the transition metal is selected from the group consisting of Cr, Mo, W, Fe, Ru, Os, Co, Rh, Ir, Ni, Pd, Pt, Au, Zn, or Cd, or a combination thereof.

* * * * *